US008370082B2

(12) United States Patent
De Peinder et al.

(10) Patent No.: US 8,370,082 B2
(45) Date of Patent: Feb. 5, 2013

(54) METHOD FOR PREDICTING A PHYSICAL PROPERTY OF A RESIDUE OBTAINABLE FROM A CRUDE OIL

(75) Inventors: Peter De Peinder, Tiel (NL); Fred Adrianus Johannes Singelenberg, Amsterdam (NL); Tom Visser, Utrecht (NL); Bert Marc Weckhuysen, Utrecht (NL)

(73) Assignee: Shell Oil Company, Houston, TX (US)

( * ) Notice: Subject to any disclaimer, the term of this patent is extended or adjusted under 35 U.S.C. 154(b) by 506 days.

(21) Appl. No.: 12/598,062

(22) PCT Filed: Apr. 25, 2008

(86) PCT No.: PCT/EP2008/055053
§ 371 (c)(1),
(2), (4) Date: Feb. 25, 2010

(87) PCT Pub. No.: WO2008/135411
PCT Pub. Date: Nov. 13, 2008

(65) Prior Publication Data
US 2010/0174494 A1    Jul. 8, 2010

(30) Foreign Application Priority Data

May 2, 2007 (EP) .................................. 07251853

(51) Int. Cl.
*G01N 31/00* (2006.01)
*G01J 5/02* (2006.01)
*G01V 3/00* (2006.01)

(52) U.S. Cl. ..................... 702/30; 250/339.07; 324/307

(58) Field of Classification Search .................... 702/30, 702/22–23, 27–29, 32, 50, 81, 84, 127–129, 702/137, 179, 182–183, 189; 250/338.1, 250/339.07, 339.11–339.12, 340, 341.1, 250/341.8; 324/307, 310, 312; 356/300, 356/303, 326; 208/15, 22, 39, 41
See application file for complete search history.

(56) References Cited

U.S. PATENT DOCUMENTS
(Continued)

FOREIGN PATENT DOCUMENTS
EP    0706040    4/1996
EP    0304232    12/1996
(Continued)

OTHER PUBLICATIONS

Blanco et al., Determination of Physico-Chemical Parameters for Bitumens Using Near Infrared Spectroscopy, 2001, Analytica Chimica Acta 434, pp. 133-141.*

(Continued)

*Primary Examiner* — Toan Le
(74) *Attorney, Agent, or Firm* — Charles W. Stewart

(57) ABSTRACT

A method for predicting a physical property of a residue obtainable from a crude oil by a process of distillation, wherein the conditions during the process are represented by a processing parameter, is disclosed. The method includes the steps of: a) using a spectroscopic technique to acquire a spectrum for the crude oil; and b) applying a predictive model based upon a correlation between the spectrum, the physical property and the processing parameter. The method may be used to predict the suitability of crude oil for bitumen production.

20 Claims, 4 Drawing Sheets

U.S. PATENT DOCUMENTS

| | | | | |
|---|---|---|---|---|
| 5,452,232 | A | | 9/1995 | Espinosa et al. ............... 702/30 |
| 5,475,612 | A | * | 12/1995 | Espinosa et al. ............. 700/268 |
| 5,712,797 | A | * | 1/1998 | Descales et al. ............... 702/30 |
| 6,070,128 | A | * | 5/2000 | Descales et al. ............... 702/30 |
| 6,477,516 | B1 | | 11/2002 | Colaiocco et al. ............. 706/21 |
| 6,490,029 | B1 | | 12/2002 | Cho et al. ....................... 356/70 |

FOREIGN PATENT DOCUMENTS

| | | |
|---|---|---|
| EP | 0859952 | 4/2003 |
| WO | WO9714953 | 4/1997 |

OTHER PUBLICATIONS

De Peinder P et al: "Prediction of long and short residue properties of crude oils from their infrared and near-infrared spectra" Applied Spectroscopy Apr. 1998 Society for Applied Spectroscopy US, vol. 62, No. 4, Apr. 2008, pp. 414-422, XP002495716 pp. 414-418.

Satya S et al: "Estimation of properties of crude oil residual fractions using chemometrics" Energy and Fuels Mar./Apr. 2007 American Chemical Society US, vol. 21, No. 2, Mar. 2007, pp. 998-1005, XP002495717 pp. 1000-p. 1002.

Falla et al: "Characterization of crude petroleum by NIR" Journal of Petroleum Science and Engineering, Elsevier, Amsterdam, NL, vol. 51, No. 1-2, Apr. 16, 2006, pp. 127-137, XP005363906 ISSN: 0920-4105 p. 133-p. 136.

International Search Report dated Sep. 12, 2008 (PCT/EP2008/055053).

* cited by examiner

METHOD FOR PREDICTING A PHYSICAL PROPERTY OF A RESIDUE OBTAINABLE FROM A CRUDE OIL

The present application claims priority from European Patent Application 07251853.3 filed 2 May 2007.

FIELD OF THE INVENTION

The invention is directed to a method for predicting a physical property of a residue obtainable from a crude oil by distillation.

BACKGROUND OF THE INVENTION

Bitumen is a complex mixture of hydrocarbons and hydrocarbon derivatives, including aliphatic, naphthenic and aromatic compounds. It is an important component in road construction and is also used in roofing, waterproofing, adhesion and sealing. It is found in nature, but is typically obtained as a product of the refining of crude oil. In the first step of the refining process, crude oil is subjected to distillation at atmospheric pressure. Fractions from the crude oil are separated according to their boiling points. The heaviest fraction is a complex mixture of high molecular weight hydrocarbons and is known as long residue. The long residue is subjected to distillation at reduced pressure in a vacuum distillation column, producing gas oil, distillate and short residue. The short residue can be used to manufacture a variety of grades of bitumen.

Bitumen has to meet a variety of quality specifications before it can be marketed. Crude oils may be assessed by the laboratory preparation of bitumen samples to ensure that the bitumen obtainable from the crude oil is marketable. Laboratory preparation of bitumen samples is a slow and laborious process, requiring large samples of the crude oil to be sent to the laboratory. The present inventors have sought to provide a simpler method whereby the suitability of crude oil for bitumen production can be assessed.

SUMMARY OF THE INVENTION

Accordingly, the present invention provides a method for predicting a physical property of a residue obtainable from a crude oil by a process of distillation, wherein the conditions during the process are represented by a processing parameter, comprising the steps of:
a) using a spectroscopic technique to acquire a spectrum for the crude oil; and
b) applying a predictive model based upon a correlation between the spectrum, the physical property and the processing parameter, wherein the correlation has been determined by a process of:
   i) selecting a set of crude oils,
   ii) using the spectroscopic technique to obtain a set of spectra for the set of crude oils,
   iii) obtaining a set of residues from the set of crude oils by a process of distillation, wherein the process conditions are varied, and recording the set of processing parameters that represent the process conditions,
   iv) measuring a set of physical properties for the set of residues, and
   v) correlating the set of spectra with the set of physical properties and the set of processing parameters by statistical analysis.

DETAILED DESCRIPTION OF THE INVENTION

Figure 2:
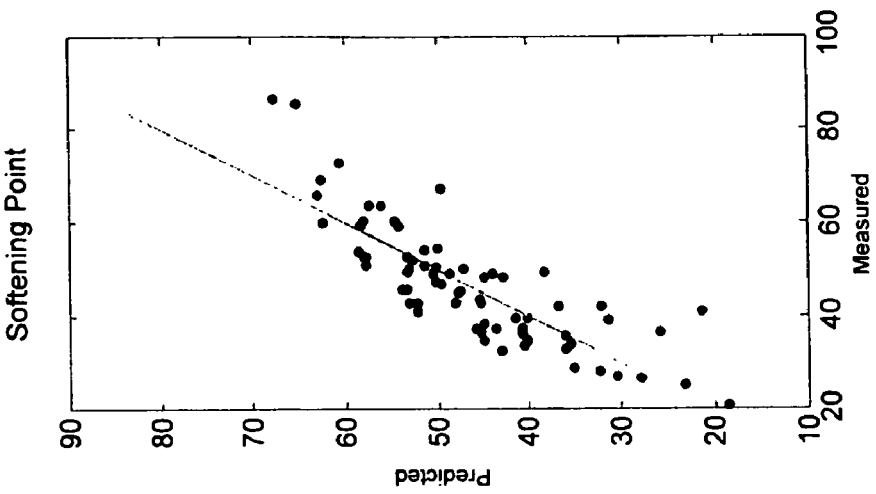
FIG. 2 is a graph showing measured softening point values versus softening point values predicted by a model.

The present inventors have developed a method wherein a simple spectroscopic analysis of a crude oil sample can be used to predict the properties of a residue. Preferably, the method is used for predicting a physical property of a short residue obtainable from a crude oil by a process of atmospheric distillation and vacuum distillation. By predicting the properties of the residue, particularly a short residue, it is possible to assess whether the crude oil is suitable for producing marketable bitumen. The method of the present invention is significantly quicker and less expensive than the known method wherein bitumen samples are prepared in the laboratory from samples of crude oil.

The predictive model used in the present invention is based upon a statistical analysis of the spectra of a set of crude oils, the physical properties of residues obtained from the set of crude oils and parameters representative of the processes used to obtain the residues.

EP 859 952 describes a method for predicting a physical property of a crude oil residue or a bituminous material by measuring the near infrared spectra of the crude oil residue or bituminous material and applying a predictive model. Unlike the present invention, this method does not enable prediction of properties by analysis of crude oil. Instead, residue or bituminous material is obtained from crude oil, and spectroscopic analysis of the residue or bituminous material is used to predict properties of the residue or bituminous material.

U.S. Pat. No. 6,477,516 describes a method for predicting a parameter of a hydrocarbon by measuring the nuclear magnetic resonance spectrum of a sample of the hydrocarbon, extracting a quantity from the spectrum and applying the extracted quantity to a neural network. The patent discusses the prediction of asphalt properties such as deformation susceptibility and penetration grade (American terminology is used, so the term asphalt equates to the term bitumen as used in the present description). However, the patent does not disclose that a predictive model can include a processing parameter representative of the process for obtaining the residue.

EP 304 232 describes a method for predicting the properties of a product and/or the yield of a product in a hydrocarbon conversion or separation process by measuring the near infrared spectra of a hydrocarbon and applying a correlation. The patent does not disclose that a predictive model can include a processing parameter representative of the process for obtaining the residue.

Spectroscopic techniques that can be used to analyse crude oil and acquire spectra are known to the person skilled in the art. The spectroscopic technique used to acquire the spectrum is preferably infrared spectroscopy, near-infrared spectroscopy, H nuclear magnetic resonance spectroscopy or $^{13}$C nuclear magnetic resonance spectroscopy. More preferably the technique is infrared spectroscopy or near-infrared spectroscopy. Most preferably the technique is infrared spectroscopy. Because volatile components in the crude oil may evaporate during spectroscopic measurements, it is preferred that the crude oil sample is contained in a closed sample cell during the measurement. For nuclear magnetic resonance spectroscopy it is preferred that the crude oil is dissolved in a deuterated solvent such as $CDCl_3$, e.g. about 50 mg crude oil in 0.5 ml $CDCl_3$.

The physical property of the residue that is predicted is preferably the density, the viscosity, the penetration or the softening point. Most preferably the physical property is the density or the viscosity. Density is typically measured at 25° C. according to the ASTM D70 standard. Viscosity is typically measured at 100° C., 135° C. or 150° C. according to the ASTM D445 standard. Penetration is typically measured at 25° C. according to the ASTM D5 standard. Softening point is typically measured using the Ring and Ball test according to the ASTM D36 standard. By predicting one or more of these physical properties it is possible for the skilled person to assess whether the crude oil is suitable for producing short residue that can be used to prepare commercially acceptable bitumen.

The method of the present invention spectroscopically analyses a crude oil and predicts a physical property of a residue that could be obtained from the crude oil by a process of distillation carried out under conditions which are represented by a processing parameter. A suitable processing parameter for representing the distillation conditions is flash depth. The flash depth is the temperature of vacuum distillation, corrected to atmospheric pressure. Therefore, in one embodiment the method of the present invention predicts a physical property of a short residue that could be obtained from the crude oil by a process of atmospheric distillation and vacuum distillation, wherein the vacuum distillation is carried out at a specified flash depth.

Another suitable processing parameter for representing the distillation conditions is the yield on short crude. Yield on short crude is a measure of the amount of residue that results from a distillation process, reported as a weight percentage or volume percentage, based upon the initial weight/volume of the long residue. The yield is a function of the distillation conditions. Yield on short crude is typically measured according to the standard ASTM D5236. Therefore, in another embodiment the method of the present invention predicts a physical property of a short residue that could be obtained from the crude oil by a process of atmospheric distillation and vacuum distillation, wherein the conditions of the vacuum distillation are set to achieve a specified yield on short crude.

The correlation between the spectrum, the physical property and the processing parameter is determined by a process of:
i) selecting a set of crude oils,
ii) using the spectroscopic technique to obtain a set of spectra for the set of crude oils,
iii) obtaining a set of residues from the set of crude oils by a process of distillation, wherein the process conditions are varied, and recording the set of processing parameters that represent the process conditions,
iv) measuring a set of physical properties for the set of residues, and
v) correlating the set of spectra with the set of physical properties and the set of processing parameters by statistical analysis.

The set of crude oils preferably consists of at least 5 crude oils, more preferably consists of at least 10 crude oils and most preferably consists of at least 20 crude oils. The set of crude oils may include blends of crude oils. The set of crude oils preferably represents a broad cross-section of available crude oils, e.g. crude oils from at least 5 different geographical regions, more preferably from at least 10 different geographical regions. Increasing the number of crude oils in the set of crude oils and increasing the variety of geographical origins in the set of crude oils may provide better data for the correlation and improve the accuracy of the predictive model.

The crude oils are spectroscopically analysed using techniques known to the person skilled in the art. A set of residues is obtained from the crude oils by distillation. Preferably a set of short residues is obtained from the crude oils by atmospheric distillation and vacuum distillation. This can be carried out using standard laboratory equipment and techniques. Different conditions, e.g. as represented by different flash depths or different yields on short crude, are used to prepare the residues. Preferably at least 3 different process conditions (as represented by the process parameter such as flash depth or yield on short crude) are used, and more preferably at least 8 different process conditions are used. Increasing the number and range of different process conditions may provide better data for the correlation and improve the accuracy of the predictive model.

The physical properties of the set of residues can be measured using standard techniques.

The correlation of the set of spectra with the set of physical properties and the set of processing parameters is carried out using statistical analysis techniques. Typically statistical analysis is performed with the aid of a computer because of the large number of calculations. The spectra are typically subjected to pre-processing. Pre-processing converts the spectral data into a suitable format for further mathematical treatment and can eliminate random effects such as noise variations and base-line shifts. Commonly applied pre-processing methods are mean-centering, auto-scaling and multiplicative scatter correction (MSC). The data is then typically analysed by methods that condense and extract information that is spread over many variables into a much smaller set of variables without losing the initial information. Techniques that can be used for this analysis include principal component analysis (PCA), partial least squares (PLS) regression, PLS discriminant analysis (PLS-DA), soft independent modelling of class analogy (SIMCA), hierarchical clustering (HC) and artificial neural networks (ANN).

In a further aspect the present invention provides a method for predicting the suitability of crude oil for bitumen production, using a method of predicting a physical property of a short residue obtainable from the crude oil according to the invention.

The invention will now be described by reference to examples which are not intended to be limiting of the invention.

Examples

Crude Oil Selection

A set of 22 crude oils was selected. The crude oils originated from a wide variety of geographical regions. The samples were stored in a refrigerator at 3° C. At least 8 hours before the spectroscopic measurement, samples were brought to ambient conditions (20° C.) Samples were homogenised at least 1 hour prior to analysis by shaking the sample bottle or can every 10 minutes.

IR-Spectroscopy

IR measurements were carried out at room temperature on a Perkin-Elmer 2000 Fourier transform spectrometer equipped with a DTGS detector. The sample compartment was flushed with dry air to reduce interference of water and $CO_2$. Spectra were recorded with a horizontal ATR accessory (MIRacle, Pike Technologies) with a ZnSe/Diamond crystal as the reflecting element. Spectral resolution was 4 $cm^{-1}$ for all spectra. A first series of spectra were recorded for the set of crude samples at 25 scan accumulations for each spectrum with medium apodisation. A second and a third series were recorded at 50 scan accumulations with medium apodisation. Recording spectra with an open sample cell revealed changes in the spectra, particularly in the fingerprint region, during a short period (~4 minutes), so all spectra were recorded using a closed sample cell.

Short Residue Preparation

Crude oil samples were subjected to atmospheric distillation according to standard ASTM D2892 to produce long residue. Long residue samples were subjected to vacuum distillation according to standard ASTM D5236 to produce short residue.

Measurement of Short Residue Properties

Penetration values for the set of short residues were measured at 25° C. according to ASTM D5. Softening points were determined using the Ring and Ball method according to ASTM D36. Density was measured according to ASTM D70. Kinematic viscosity was measured according to ASTM D445.

Correlation of Results: IR Spectra, Short Residue Properties and Flash Depth

The IR spectra were pre-processed using Principal Component Analysis (PCA) and the first 10 scores from the PCA model were used to describe each spectrum. The 10 scores and flash depth temperature provided a data matrix X. The short residue properties were used as a data matrix Y. A partial least squares (PLS) regression of data matrix X against data matrix Y was carried out.

The RMSECV (root-mean-square error of validation) values and the corresponding number of LVs (latent variables) for each of the short residue properties are shown in Table 1:

| Short Residue Property | Units | Mean Value | RMSECV | LVs |
| --- | --- | --- | --- | --- |
| Log (Penetration) | Log (0.1 mm) | 1.68 | 0.21 | 3 |
| Softening point | ° C. | 46.69 | 8.62 | 2 |
| Density | kg/l | 1.0045 | 0.0083 | 3 |
| Viscosity | $mm^2$/s | 42.52 | 1.26 | 2 |

Figure 1:
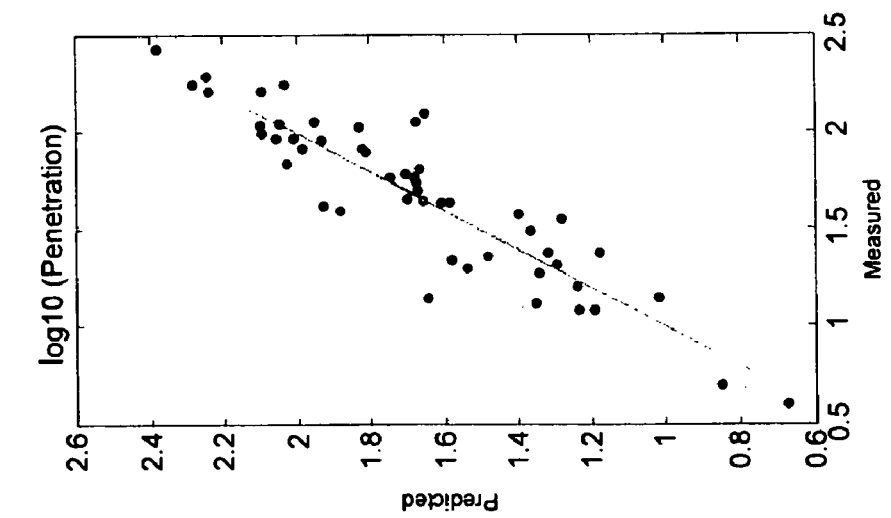
FIG. 1 is a graph showing measured penetration values versus penetration values predicted by a model.
Figure 4:
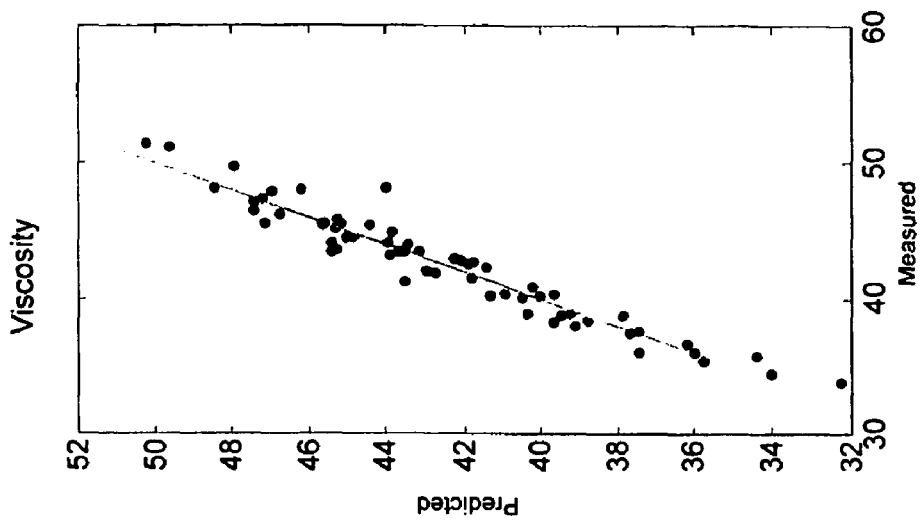
FIG. 4 is a graph showing measured viscosity values versus viscosity values predicted by a model.
Figure 3:
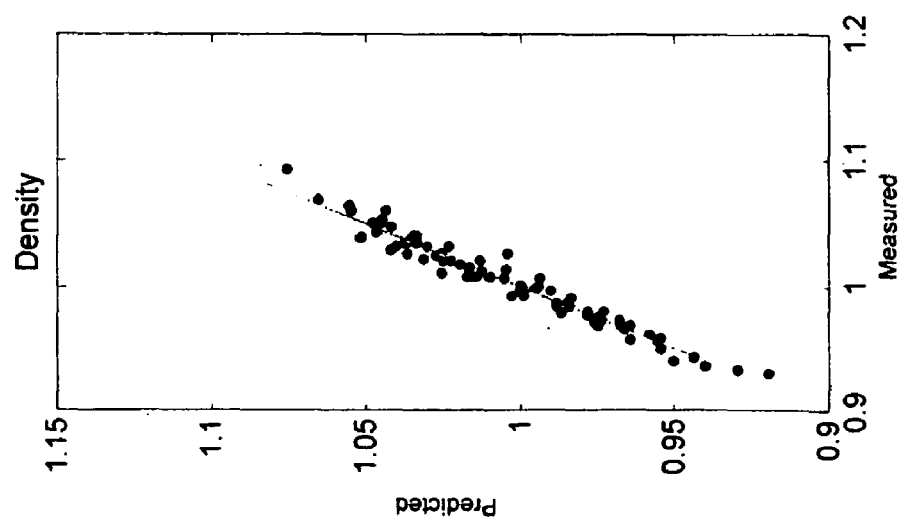
FIG. 3 is a graph showing measured density values versus density values predicted by a model.

The lower the RMSECV value the better a model predicts the property. The more LVs are used the more complex the model gets and the risk of over fitting (adding noise) increases. Plots of the measured properties of penetration, softening point, density and viscosity versus the values predicted by the model are shown in FIGS. 1-4. The graphs show successful predictions for all four properties, with particularly successful prediction for density and viscosity.

Correlation of Results: IR Spectra, Short Residue Properties and Yield on Short Crude The first 10 scores from the PCA model were used to describe each IR spectrum. The 10 scores and yield on short crude value provided a data matrix X. The short residue properties were used as a data matrix Y. A partial least squares (PLS) regression of data matrix X against data matrix Y was carried out.

The RMSECV (root-mean-square error of validation) values and the corresponding number of LVs (latent variables) for each of the short residue properties are shown in Table 2:

| Short Residue Property | Units | Mean Value | RMSECV | LVs |
| --- | --- | --- | --- | --- |
| Log (Penetration) | Log (0.1 mm) | 1.68 | 0.38 | 3 |
| Softening point | ° C. | 46.69 | 9.46 | 3 |
| Density | kg/l | 1.0045 | 0.0136 | 3 |
| Viscosity | $mm^2$/s | 42.52 | 1.87 | 3 |

Figure 6:
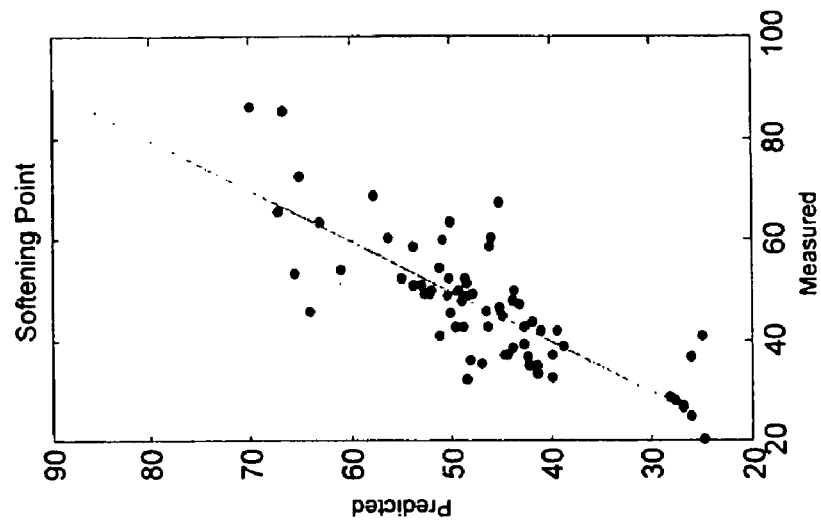
FIG. 6 is a graph showing measured softening point values versus softening point values predicted by a model.
Figure 5:
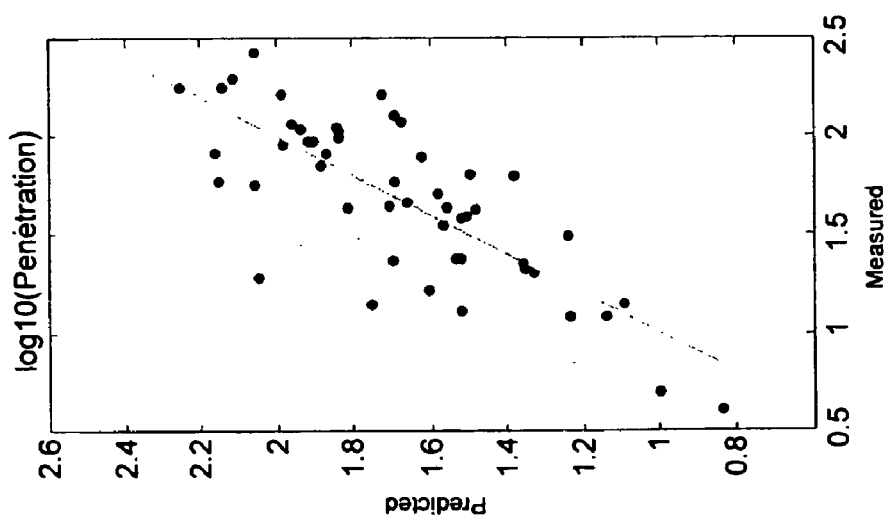
FIG. 5 is a graph showing measured penetration values versus penetration values predicted by a model.
Figure 8:
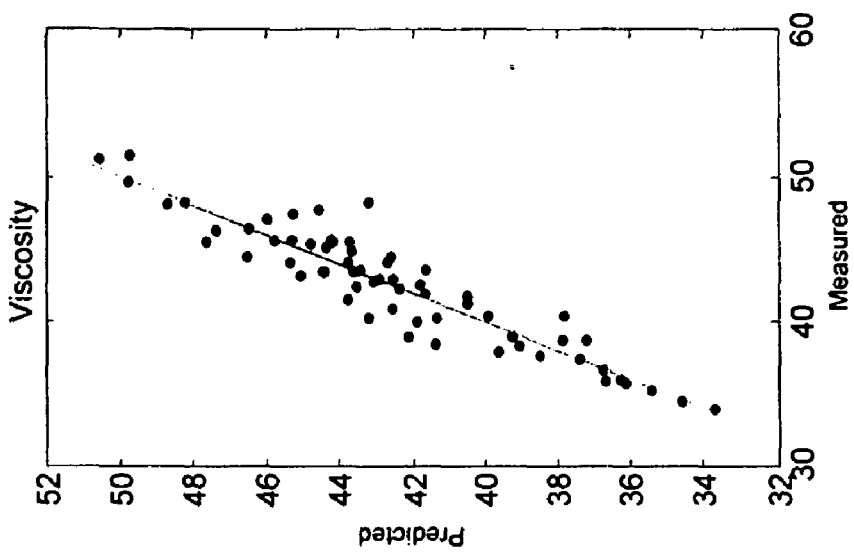
FIG. 8 is a graph showing measured viscosity values versus viscosity values predicted by a model.
Figure 7:
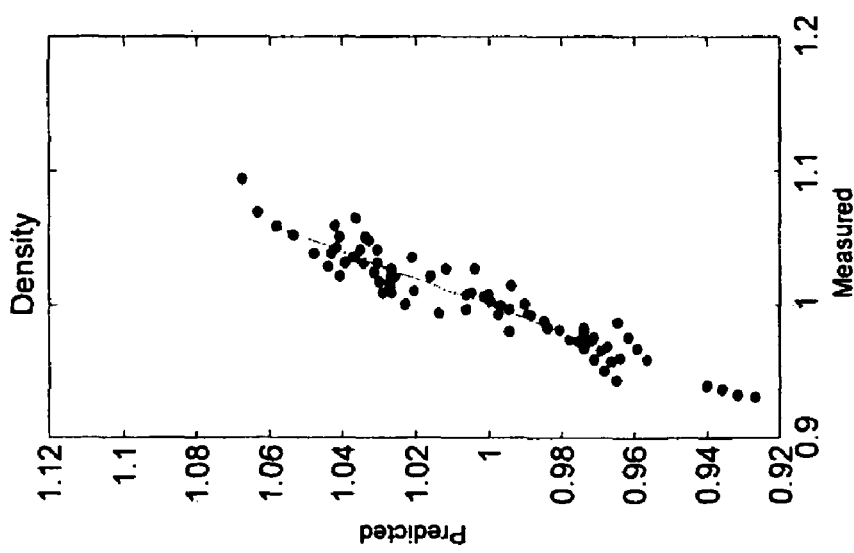
FIG. 7 is a graph showing measured density values versus density values predicted by a model.

Plots of the measured properties of penetration, softening point, density and viscosity versus the values predicted by the model are shown in FIGS. 5-8. Again, successful predictions are shown for all four properties, although the RMSECV values are slightly higher than for the correlation based upon flash depth.

What is claimed is:

1. A method for predicting a physical property of a residue obtainable from a crude oil by a process of distillation, wherein the conditions during the process are represented by a processing parameter, comprising the steps of:
   a) using a spectroscopic technique to acquire a spectrum for the crude oil; and
   b) applying a predictive model to the spectrum and the processing parameter, wherein the predictive model is based upon a correlation between the spectrum, the physical property and the processing parameter, wherein the correlation has been determined by a process of:
      i) selecting a set of crude oils,
      ii) using the spectroscopic technique to obtain a set of spectra for the set of crude oils,
      iii) obtaining a set of residues from the set of crude oils by a process of distillation, wherein the process conditions are varied, and recording the set of processing parameters that represent the process conditions,
      iv) measuring a set of physical properties for the set of residues, and
      v) correlating the set of spectra with the set of physical properties and the set of processing parameters by statistical analysis; and
   whereby the physical property of the residue is predicted.

2. The method according to claim 1, wherein the residue is a short residue and the process of distillation is a process of atmospheric distillation and vacuum distillation.

3. The method according to claim 2, wherein the spectroscopic technique used to acquire a spectrum is infrared spectroscopy, near-infrared spectroscopy, $^1$H nuclear magnetic resonance spectroscopy or $^{13}$C nuclear magnetic resonance spectroscopy.

4. The method according to claim 3, wherein the spectroscopic technique is infrared spectroscopy or near-infrared spectroscopy.

5. The method according to claim 4, wherein the physical property is the density, the viscosity, the penetration or the softening point.

6. The method according to claim 3, wherein the physical property is the density, the viscosity, the penetration or the softening point.

7. The method according to claim 3, wherein the processing parameter representative of the process conditions is the flash temperature.

8. The method according to claim 2, wherein the physical property is the density, the viscosity, the penetration or the softening point.

9. The method according to claim 2, wherein the processing parameter representative of the process conditions is the flash temperature.

10. The method according to claim 1, wherein the spectroscopic technique used to acquire a spectrum is infrared spectroscopy, near-infrared spectroscopy, $^1$H nuclear magnetic resonance spectroscopy or $^{13}$C nuclear magnetic resonance spectroscopy.

11. The method according to claim 10, wherein the spectroscopic technique is infrared spectroscopy or near-infrared spectroscopy.

12. The method according to claim 11, wherein the physical property is the density, the viscosity, the penetration or the softening point.

13. The method according to claim 11, wherein the processing parameter representative of the process conditions is the flash temperature.

14. The method according to claim 11, wherein the physical property is the density, the viscosity, the penetration or the softening point.

15. The method according to claim 10, wherein the processing parameter representative of the process conditions is the flash temperature.

16. The method according to claim 1, wherein the physical property is the density, the viscosity, the penetration or the softening point.

17. The method according to claim 16, wherein the processing parameter representative of the process conditions is the flash temperature.

18. The method according to claim 1, wherein the processing parameter representative of the process conditions is the flash temperature.

19. The method according to claim 1, wherein the processing parameter representative of the process conditions is the yield on short crude.

20. The method for predicting the suitability of crude oil for bitumen production, comprising a step of predicting a physical property of a residue obtainable from the crude oil according to claim 1.

* * * * *